(12) United States Patent
Roy et al.

(10) Patent No.: US 8,502,975 B2
(45) Date of Patent: Aug. 6, 2013

(54) STANDOFF DETERMINATION OF THE SIZE AND CONCENTRATION OF LOW CONCENTRATION AEROSOLS

(75) Inventors: Gilles Roy, Shannon (CA); Nathalie Roy, Quebec (CA)

(73) Assignee: Her Majesty the Queen in Right of Canada as Represented by the Minister of Defence, Ottawa, Ontario (CA)

( * ) Notice: Subject to any disclaimer, the term of this patent is extended or adjusted under 35 U.S.C. 154(b) by 207 days.

(21) Appl. No.: 13/063,953

(22) PCT Filed: Sep. 14, 2009

(86) PCT No.: PCT/CA2009/001243
§ 371 (c)(1),
(2), (4) Date: May 16, 2011

(87) PCT Pub. No.: WO2010/031161
PCT Pub. Date: Mar. 25, 2010

(65) Prior Publication Data
US 2011/0317161 A1 Dec. 29, 2011

Related U.S. Application Data

(60) Provisional application No. 61/097,441, filed on Sep. 16, 2008.

(51) Int. Cl.
*G01N 15/02* (2006.01)

(52) U.S. Cl.
USPC .......................................... 356/336; 356/335

(58) Field of Classification Search
USPC ............ 356/335–343, 28, 28.5, 3, 4.01, 5.05, 356/5.08
See application file for complete search history.

(56) References Cited

U.S. PATENT DOCUMENTS
7,391,506 B2 * 6/2008 Harris et al. ................. 356/28.5
* cited by examiner

*Primary Examiner* — Tri T Ton
(74) *Attorney, Agent, or Firm* — Michael R. Williams; Ade & Company Inc.

(57) ABSTRACT

A Multiple-Field-Of-View (MFOV) lidar is used to characterize the size and concentration of low concentration of bioaerosol particles. The concept relies on the measurement of the forward scattered light by using the background aerosols at various distances at the back of the sub-visible cloud. It also relies on the subtraction of the background aerosol forward scattering contribution and on the partial attenuation of the first order backscattering. We demonstrate theoretically and experimentally that the MFOV lidar can measure with a good precision the effective diameter of low concentration bioaerosol clouds.

3 Claims, 8 Drawing Sheets

STANDOFF DETERMINATION OF THE SIZE AND CONCENTRATION OF LOW CONCENTRATION AEROSOLS

PRIOR APPLICATION INFORMATION

This application claims the benefit of U.S. Provisional Patent Application 61/097,441, filed Sep. 16, 2008.

BACKGROUND OF THE INVENTION

The knowledge of aerosols particle size and concentration is highly relevant for many applications dealing with aerosols such as the dissemination of insecticides and the emission of stacks. In the defense and security area, the standoff detection of bioaerosol clouds with spectrometric LIDAR is now a reality (Simard et al., 2004, IEEE Trans. On Geoscience and Remote Sensing 42: 865-874). This technique has the advantages of rapidly monitoring the atmosphere over a wide area without physical intrusions and reporting an approaching threat before it reaches sensitive sites. However, the lack of information on bioaerosols particle size does not permit accurate measurement of the concentration. The knowledge of the size could also be used to reduce the rate of false alarm since pollens are significantly larger than bioaerosols agents. With the Multiple-Field-Of-View (MFOV) lidar developed at DRDC Valcartier, we have already demonstrated that the multiple scattering of a laser beam propagating in the atmosphere contains information on the size of the aerosols (*Lidar: Range-Resolved Optical Remote Sensing of the Atmosphere, chapter 3: Lidar and Multiple Scattering*, Editor Claus Weikamp (Springer Series in Optical Sciences), 2005, 455 pp, ISBN 0-387-40075; N. Roy et al., 2004, "Measurement of the azimuthal dependence of cross-polarized lidar returns and its relation to optical depth," *Appl. Opt.* 43, 2777-2785).

These innovative results and recent developments with gated-ICCD (Intensified Charged Coupled Device) cameras have led us to perform a preliminary investigation on the determination of background aerosols and bioaerosols size and concentration. The difficulty with bioaerosol clouds is that they are sub-visible and therefore their low concentrations do not produce strong multiple scattering signals. In addition, they are mixed with background aerosols. In this paper, we demonstrate that it is possible to obtain size information on low concentration of bioaerosols using the MFOV lidar principle and the concept of background aerosol subtraction. We present the theory of the concept and demonstrate experimentally its validity on effective diameter retrieval of Elm and Timothy low concentration pollens.

SUMMARY OF THE INVENTION

According to an aspect of the invention, there is provided a method of determining diameter of particles in a low concentration cloud or optical depth of a low concentration cloud comprising:

measuring scattering of a low concentration cloud comprised of particles of interest using a multiple field of view light detection and ranging (MFOV lidar) system, calculating the double scattering cloud signal and the single scattering cloud signal from said measurement and normalizing the double scattering cloud signal and the single scattering cloud signal, thereby providing a normalized cloud signal;

measuring scattering of a background region using a MFOV lidar system, calculating the double scattering background signal and the single scattering background signal from said measurement and normalizing the double scattering background signal and the single scattering background signal, thereby providing a normalized background signal;

subtracting the normalized background signal from the normalized cloud signal, and using said subtracted signal to calculate encircled energy of the particles within the low concentration cloud and optical depth of the low concentration cloud; and determining the effective particle diameter from the maximum encircled energy of the particles.

In some embodiments, the cloud signal and the background signal are normalized or averaged.

In some embodiments, the MFOV lidar system includes a transmission mask for attenuating central fields of view of the MFOV lidar system.

The transmission mask may have a 1% transmission for FOVs smaller than 1.32 mrad and a 94% transmission for FOVs larger than 1.32 mrad. Preferably, the transmission mask is positioned in the image plane and is large enough to cover the laser beam size and the transmission is low enough to make the measured attenuated laser beam energy close to the measured scattered energy signal.

BRIEF DESCRIPTION OF THE DRAWINGS

FIG. 1*a* shows second order scattering detected at an angle θ by the MFOV lidar; the ellipses represent the phase functions. FIG. 1*b* illustrates two equivalent possibilities for a second order back scattering event: 1) a forward scattering followed by a backscattering and 2) a backscattering followed by a forward scattering.

for effective diameters of 10 μm, 20 μm and 30 μm.

Figure 3:
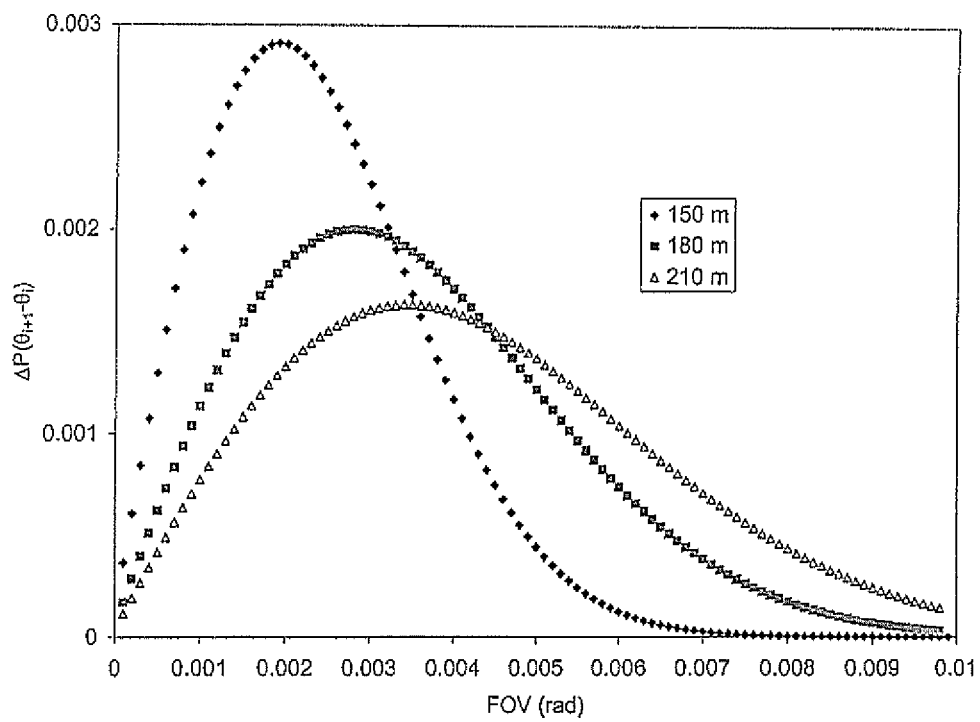

FIG. 3. Encircled energies $\Delta P_{Norm}(\theta_{i+1} - \theta_i)$ as a function of $$\frac{(\theta_{i+1} + \theta_i)}{2}$$

for an effective diameter of 30 μm for three sounding distances.

Figure 4:
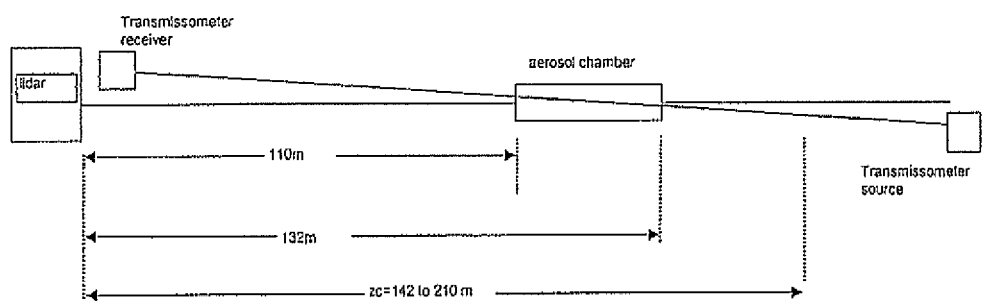
Figure 5:
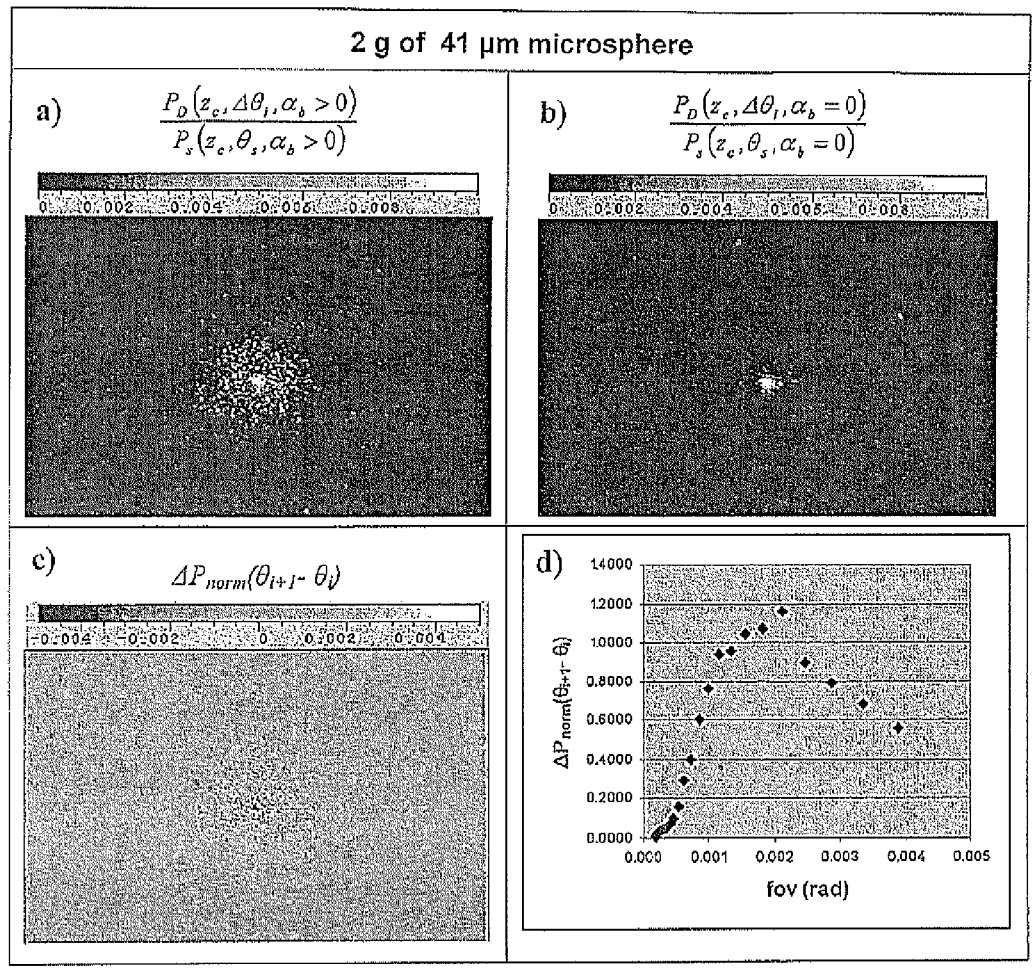

FIG. 4 illustrates the experimental set-up used to validate the concept presented above in order to determine the size and concentration of low concentration bioaerosol clouds FIG. 5. FIG. 5*a* shows the normalized lidar return on background aerosols obtained when 2 g of M6001AE were disseminated inside the aerosol chamber; FIG. 5*b* shows the same measurement in absence of disseminated material inside the chamber; FIG. 5*c*=FIG. 5*b*-FIG. 5*a* and FIG. 5*d* illustrated the image analysis in term of encircled energy in logarithmic spaced rings delimited by $\theta_i$ and $\theta_{i+1}$ FIG. 6. Number and volume density distribution for trimodal lognormal distributions.

Figure 7:
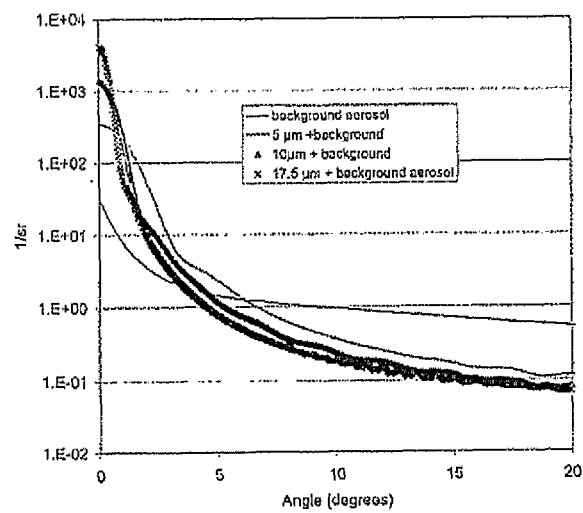

FIG. 7. Phase function as a function of the scattering angle.

Figure 8:
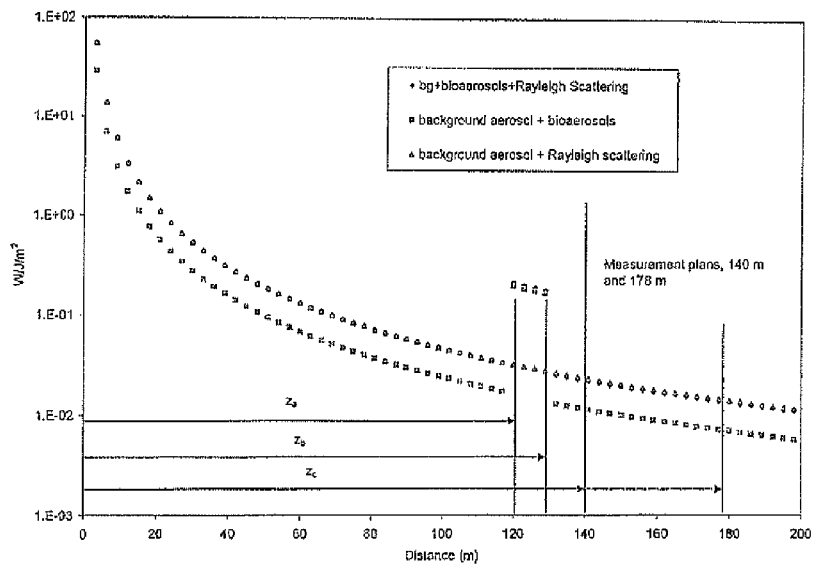

FIG. 8. Single scattering lidar return as a function of distance from the lidar system.

Figure 9:
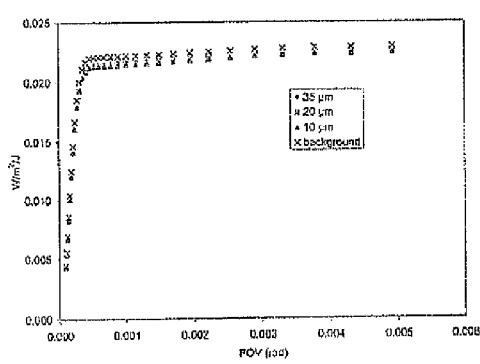

FIG. 9. Lidar encircled energy return as a function of FOV at a sounding distance of 140 m.

Figure 10:
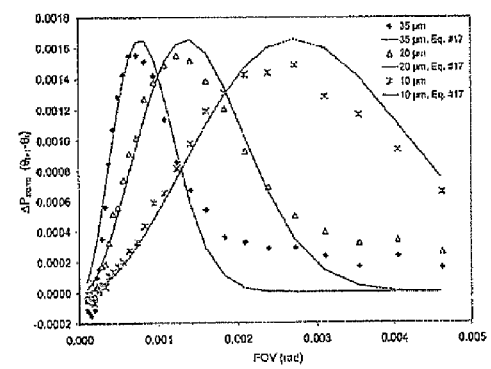

FIG. 10. $\Delta P_{norm}(z_c, \theta_{i+1} - \theta_i)$ as a function of $0.5(\theta_{i+1} - \theta_i)$ for a sounding distance of 140 m for the 10, 20, and 35 μm particles.

Figure 11:
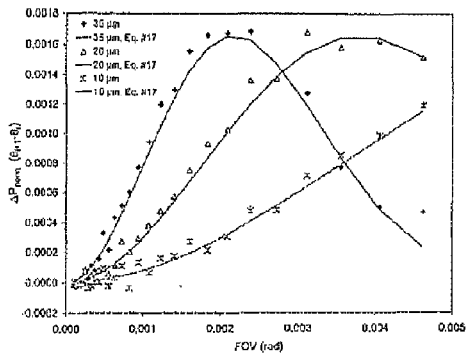

FIG. 11. $\Delta P_{norm}(Z_c, \theta_{i+1}-\theta_i)$ as a function of $0.5(\theta_{i+1}-\theta_i)$ for a sounding distance of 178 m for the 10, 20 and 35 µm particles.

Figure 12:
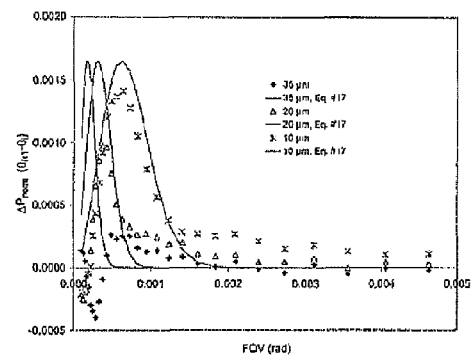

FIG. 12. $\Delta P_{norm}(Z_c, \theta_{i+1}-\theta_i)$ as a function of $0.5(\theta_{i+1}-\theta_i)$ for a sounding distance of 1025 m for the 10, 20 and 35 µm particles.

Figure 13:
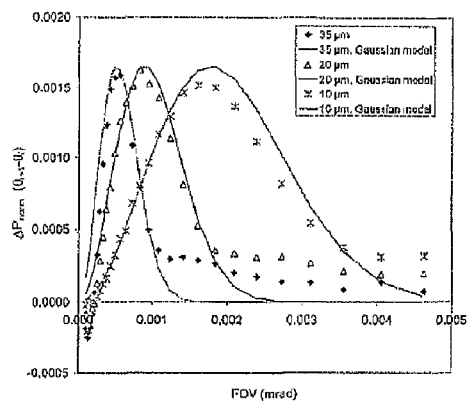

FIG. 13. $\Delta P_{norm}(Z_c, \theta_{i+1}-\theta_i)$ as a function of $0.5(\theta_{i+1}-\theta_i)$ for a sounding distance of 1075 m for the 10, 20 and 35 µm particles.

Figure 14:
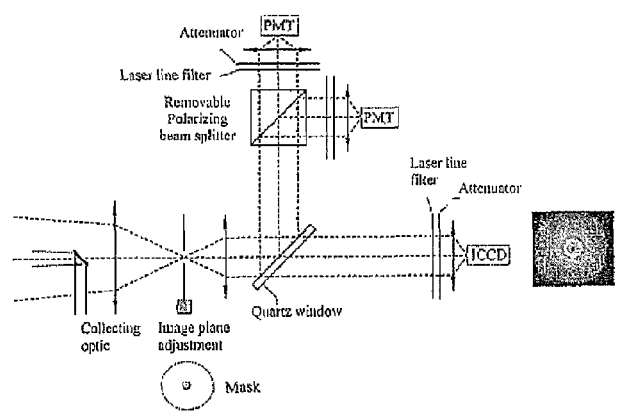

FIG. 14. MFOV imaging lidar.

Figure 15:
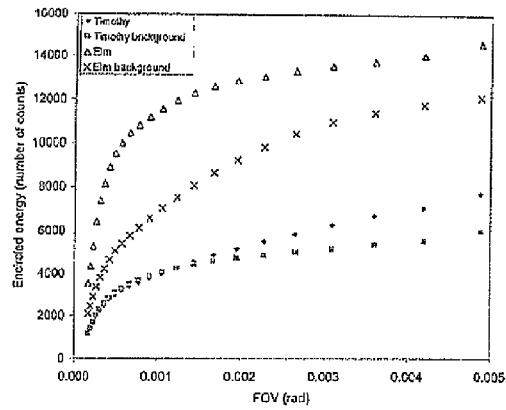

FIG. 15. Encircled energy as a function of FOVs for the Elm and Timothy pollens for sounding measurement distances of 158 and 178 m, respectively.

Figure 16:
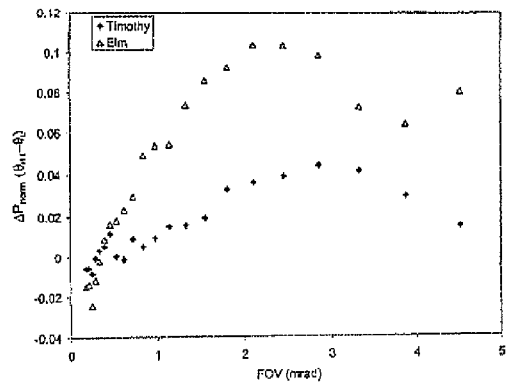

FIG. 16. Measured normalized $\Delta P_{norm}(Z_c, \theta_{i+1}-\theta_i)$ for the Elm and Timothy pollens for sounding measurements distances of 158 and 178 m respectively.

Figure 17:
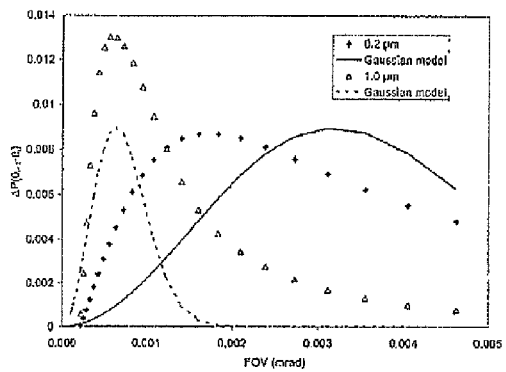

FIG. 17. $\Delta P_{norm}(Z_c, \theta_{i+1}-\theta_i)$ as a function of $0.5(\theta_{i+1}-\theta_i)$ for sounding distances of 4010 m for 0.2 and 1 µm particles.

Figure 18:
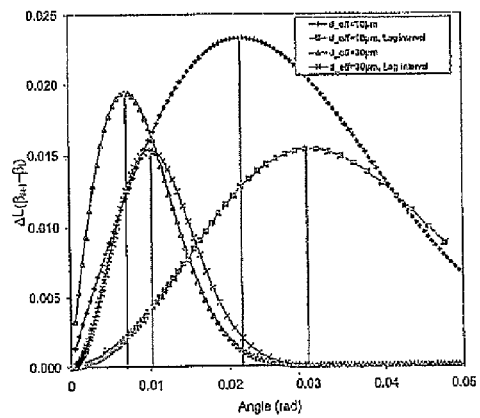

FIG. 18. Scattered energy in a ring as a function of scattering angle for linear and logarithmic spacing of the interval.

DESCRIPTION OF THE PREFERRED EMBODIMENTS

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

Herein, it is demonstrated that Multiple-Field-Of-View (MFOV) lidar signals can be used to determine the effective diameter and the optical depth of low concentration clouds. While in one example, pollen clouds are used, it is of note that any bioaerosol cloud can be examined and analyzed using the described method. As will be appreciated by one of skill in the art, the term 'bioaerosol cloud' is well understood in the art. For example, a 'bioaerosol cloud' may be considered to be a cloud or plume comprising an airborne chemical agent or biological agent that is either man-made or the result of a process or purified, isolated or collected by man. It is of note that prior art techniques cannot measure particle size and concentration of low concentration bioaerosol clouds. The bioaerosol cloud may also be considered as a low concentration cloud or 'thin' cloud within the atmosphere. Specifically, multiple wavelength lidar (Light Detection and ranging) techniques are not suitable because the particles are larger than the probing wavelength. Furthermore, standard multiple scattering techniques do not work because the signal from the multiple scattering contributions of the bioaerosol cloud is buried in 'noise'.

As discussed below, the technique relies on three concepts:
The measurement of the second-order forward scattered light on background aerosols at the back of the sub-visible bioaerosol cloud;
The subtraction of the contribution of background aerosol forward scattering and
The partial attenuation of the first order backscattering.

The recovery of the effective size parameter is easily achieved by the application of a simple mathematical formula that requires knowledge of basic lidar information such as the cloud distance and the sounding depth and two measurements realized with an MFOV imaging lidar. The first lidar measurement is done in the presence of bioaerosols, while the second is used to quantify background aerosols. Once the effective diameter is known, the optical depth can be easily obtained using a simple mathematical formula that requires the same basic knowledge as for the size of the parameter retrieval. We have also demonstrated that the recovery technique developed for bioaerosol standoff can be extended to other applications such as the study and characterization of cirrus clouds and plumes.

In one aspect of the invention, there is provided a method of determining diameter of particles in a low concentration cloud or optical depth of a low concentration cloud comprising:

measuring scattering of a low concentration cloud comprised of particles of interest using a multiple field of view light detection and ranging (MFOV lidar) system, calculating the double scattering cloud signal and the single scattering cloud signal from said measurement and normalizing the double scattering cloud signal and the single scattering cloud signal, thereby providing a normalized cloud signal;

measuring scattering of a background region using a MFOV lidar system, calculating the double scattering background signal and the single scattering background signal from said measurement and normalizing the double scattering background signal and the single scattering background signal, thereby providing a normalized background signal;

subtracting the normalized background signal from the normalized cloud signal, and using said subtracted signal to calculate encircled energy of the particles within the low concentration cloud and optical depth of the low concentration cloud; and determining the effective particle diameter from the maximum encircled energy of the particles.

As will be appreciated by one of skill in the art, a low concentration cloud refers to for example a bioaerosol cloud, that is, a 'thin' cloud, that is, a cloud with a narrow or relatively thin or small optical depth comprised of a low concentration of particles.

As used herein, 'background' refers to a region of the atmosphere lacking the low concentration cloud or bioaerosol cloud.

In some embodiments, the cloud signal and the background signal are normalized or averaged.

In some embodiments, the MFOV lidar system includes a transmission mask for attenuating central fields of view of the MFOV lidar system. Preferably, the mask is large enough to cover the laser beam size and the transmission may be low enough to make the measured attenuated laser beam energy close to the measured scattered energy signal.

As an example, the transmission mask may have a 1% transmission for FOVs smaller than 1.32 mrad and a 94% transmission for FOVs larger than 1.32 mrad. Preferably, the transmission mask is positioned in the image plane. In other embodiments, there is provided a MFOV lidar system comprising a transmission mask positioned in the image plane.

As discussed below, in the instant method, the second order scattering is calculated using data from the MFOV lidar. The second order scattering is also normalized to the first order scattering and in some embodiments the first order scattering is attenuated using a mask with a low transmission central zone which allows maximization of the signal to noise ratio in the larger fields of view. As discussed herein, the subtraction of a background signal from the signal from the bioaerosol cloud removes 'noise' which would otherwise mask the signal from the low concentration cloud or bioaerosol cloud. As discussed below, this information is used to calculate the optical depth of the bioaerosol cloud and encircled energy of the particles within the cloud which is in turn used to calculate the effective diameter and concentration of the particles within the cloud. It is of note that the bioaerosol cloud of interest is typically at least 100 m from the MFOV lidar system.

Figure 1:
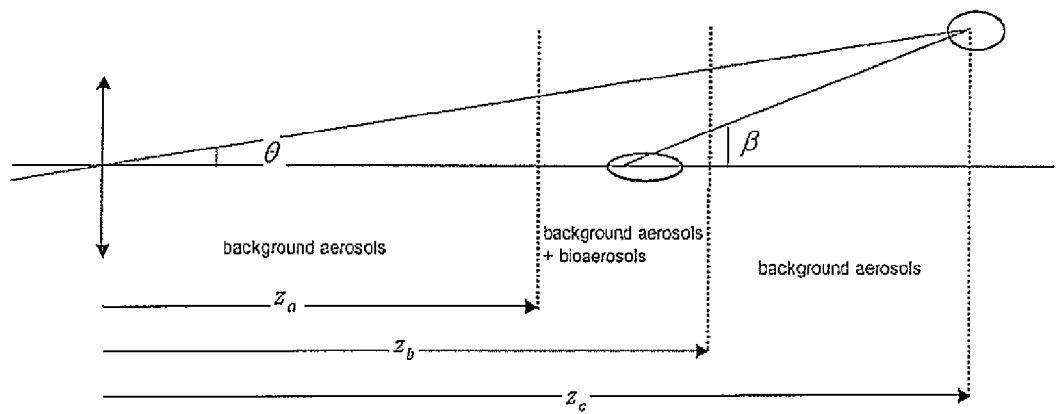
FIG. 1.
Figure 1:
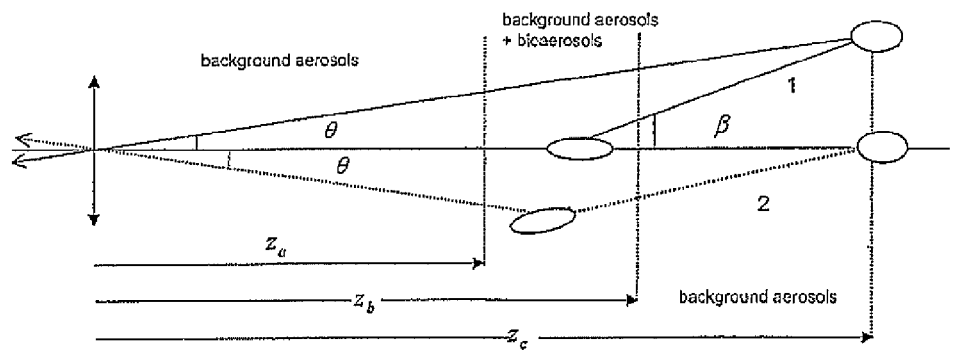

FIGS. 1a and 1b illustrates the MFOV lidar basic principle based on second order scattering: a first forward scattering occurs at an angle β which is followed by a backscattering collected by the telescope at an angle θ. The single scattering lidar can be represented by the following equation:

$$P_s(z_c) = P_0 \frac{c\tau}{2} \frac{A}{z_c^2}(\alpha_s(z_c))p(r, z_c, \beta = \pi)e^{-2\int_0^{z_c}\alpha(z)dz} \quad [1]$$

where as usual, $P_0$ is the laser pulse power, c the speed of light, τ the pulse duration, A the area of the collecting optic, $z_c$ the sounding distance, α and $\alpha_s$ are respectively the extinction and scattering extinction coefficient and $p(r, z_c, \beta=\pi)$ the value of the phase function for a scattering angle β of 180°.

The essence of the multiple-field-of-view lidar technique (G. Roy et al., 1999, *Appl. Opt.* 38, 5202-5211) is the measurement of the scattered power as a function of the receiver field of view θ. The scattered power contains information on scatters size. In FIG. 1a, the angle θ corresponds to one half of the total lidar FOV. We consider that the laser beam divergence is small and that the scattered power originating from single scattering events is concentrated inside the smallest field of view $\theta_{min}$ of the detector. We also assume that the extinction and the particles size distribution of the atmospheric aerosols are spatially homogeneous, and that the time delay of the scattered photons is negligible. The scattered power in the FOV interval $\Delta\theta_i = \theta_{i+1}-\theta_i$ coming from second scattering order can be calculated using:

$$P_D(z_c, \Delta\theta_i) = P_0 e^{-2\int_0^{z_c}\alpha(z)dz}\frac{c\tau}{2}\frac{A}{z_c^2}2$$
$$\int_0^{z_c}\int_0^{2\pi}\int_{\beta_i}^{\beta_{i+1}}[\alpha_s(z)p(r, z, \beta)][\alpha_s(z_c)p(r, z_c, \beta_{back})]\sin\beta d\beta d\phi dz \quad [2]$$

The factor 2 in front of the integral is coming from the reciprocity theorem (L. Katsev et al., 1997, *J. Opt. Soc. Am. A* 14, 1338-1346), $\alpha_s$ is the scattering extinction coefficient, $p(r, z, \beta)$ and $p(r, z_c, \beta_{back})$ are the values of the phase function for the forward (β) and backward ($\beta_{back}=\pi-\beta+\theta$) scattering angles for a particle of radius r, $z_a$ and $z_b$, are the distances delimiting the bioaerosol cloud, $z_c$ is the distance where the scattered radiation is measured, the quantity $[\alpha_s(z)p(r, z, \beta)]$ represents the forward scattering coefficient while $[\alpha_s(z_c)p(r, z_c, \beta_{back})]$ represents the backscattering coefficient, and φ is the azimuthal angle ranging from 0 to 2π. The FOV θ is easily related to the scattering angle β in a simple geometric relation:

$$\tan\beta = \frac{z_c\tan\theta}{z_c - z}.$$

Now, considering that $p(r, z_c, \beta_{back})$ is quasi-uniform over the backscattering angles of interest, we can set its value equal to p(r, $z_c$, $\beta=\pi$). We also use the concept of encircled energy (Born and Wolf, *Principles of Optics*, chap 8, Pergamon press, Oxford, 1975) which is defined:

$$\Delta L(r, z, \beta_{i+1} - \beta_i) \equiv \int_{\beta_i}^{\beta_{i+1}}\int_0^{2\pi} p(r, z, \beta)\sin\beta d\beta d\varphi \quad [3]$$

as the fraction of the energy contained in the ring delimited by $\beta_i$ and $\beta_{i+1}$.

Normalization of the double scattering signal with the single scattering signal, $P_S(z_c, \theta_s)$ leads to:

$$\frac{P_D(z_c, \theta_{i+1} - \theta_i)}{P_S(z_c, \theta_s)} = 2\int_0^{z_c}(\alpha_s(z)\Delta L(r, z, \beta_{i+1} - \beta_i)dz \quad [4]$$

where $\theta_s$ corresponds to the angle used for the measurement of the single scattering signal.

The measurement technique requires two measurements: one in presence of the bioaerosol cloud in the interval [$z_a$, $z_b$] and a second in its absence. The objective is to subtract the second signal from the first in order to minimize the effect of background aerosols on the bioaerosols size and concentration measurement.

The integral over $z_c$ is broken down in 3 intervals: [0, $z_a$], [$z_a$, $z_b$] and [$z_b$, $z_c$] as illustrated in FIG. 1a.

In the absence of bioaerosols, we have for the intervals [0, $z_a$], [$z_a$, $z_b$] and [$z_b$, $z_c$]:

$$\alpha_s(z)p(r,z,\beta)=\alpha_a(z)\omega_{0a}p_a(r,\beta)+\alpha_R p_R(r,\beta) \quad [5]$$

and in the presence of bioaerosols in the interval [$z_a$, $z_b$] we have:

$$\alpha_s(z)p(r,z,\beta)=\alpha_a(z)\omega_{0a}p_a(r,\beta)+\alpha_b(z)\omega_{0b}p_b(r,\beta)+\alpha_R p_R(r,\beta) \quad [6]$$

where:

$\alpha_a$, $p_a$(r, $\beta$) are the background aerosols extinction coefficient and phase function;

$\alpha_b$, $p_b$(r, $\beta$) are the bioaerosols extinction coefficient and phase function;

$\alpha_R$, $p_R$(r, $\beta$) are the Rayleigh scattering coefficient and phase function;

$\overline{\omega}_{0a}$ and $\overline{\omega}_{0b}$ are the respective single scatter albedo for background aerosols and bioaerosols.

Using eq.4 to eq.6 and subtracting the normalized background aerosols signal, we find $$\Delta P_{Norm}(\theta_{i+1} - \theta_i) = \frac{P_D(z_c, \theta_{i+1} - \theta_i, \alpha_b > 0)}{P_s(z_c, \theta_s, \alpha_b > 0)} - \frac{P_D(z_c, \theta_{i+1} - \theta_i, \alpha_b = 0)}{P_s(z_c, \theta_s, \alpha_b = 0)} = 2\varpi_{0b}\int_{z_a}^{z_b}\alpha_b\Delta L(r, z, \beta_{i+1} - \beta_i)dz \quad [7]$$

This is the key equation that relates the normalized double scattering measurement to the bioaerosol cloud optical depth and the encircled energy. The measurement of $\Delta P_{Norm}(\theta_{i+1}-\theta_i)$ can, in principle, provides information on the size and the concentration of the bioaerosols. In order to recover bioaerosols size information from eq.7, we parameterize the phase function of a unimodal bioaerosols size distribution with a Gaussian fit using the definition of effective diameter as suggested by Bissonnette (L. Bissonnette, 1995, *Appl. Opt.* 33, 6449-6465):

$$p(\beta) = \frac{A_2}{\pi\omega_{0b}}y^2e^{-A_1^2y^2\beta^2} \quad [8]$$

$$y = \frac{\pi d_{eff}}{\lambda};\ A_1 = 0.544;\ A_2 = 0.139$$

where the effective diameter has been defined as a function of particles radius r as:

$$d_{eff}=2\langle r^3\rangle/\langle r^2\rangle$$

After substitution in eq. 3 and using the small angle approximation, we get $$\Delta L(\beta_{i+1} - \beta_i) = \frac{2A_2 y^2}{\omega_{0b}} \int_{\beta_i}^{\beta_{i+1}} e^{-A_1^2 y^2 \beta^2} \beta \, d\beta \qquad [9]$$

Figure 2:
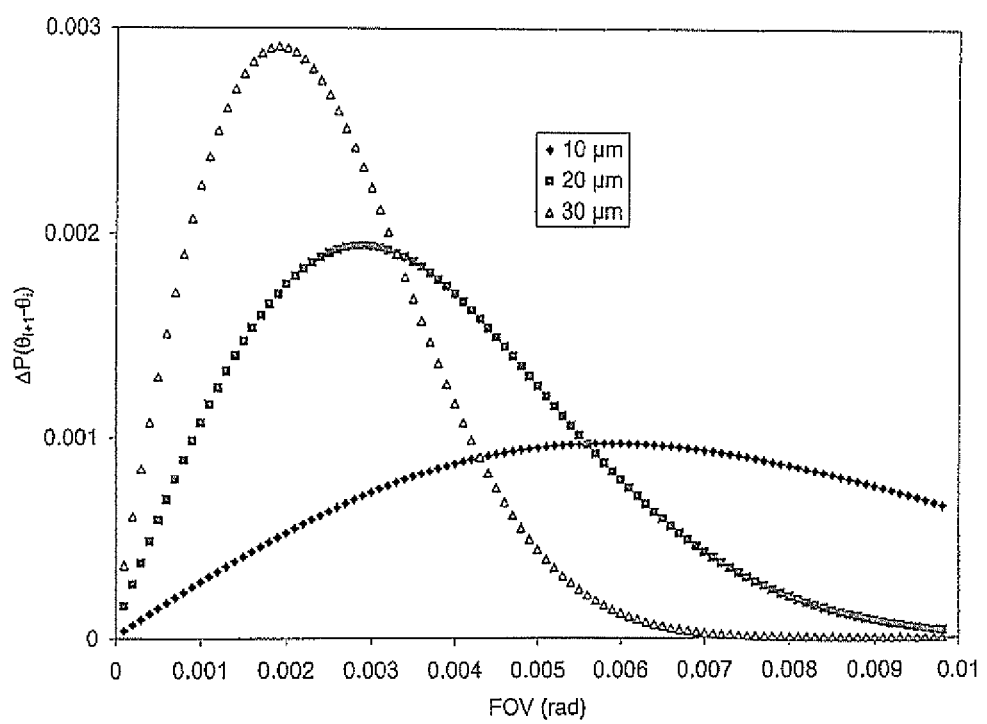
FIG. 2. Encircled energies $\Delta P_{Norm}(\theta_{i+1} - \theta_i)$ as a function of $$\frac{(\theta_{i+1} + \theta_i)}{2}$$

By substituting eq.9 in eq.7, we can easily calculate $\Delta P_{Norm}$ ($\theta_{i+1} - \theta_i$) for various aerosols sizes and cloud distance geometries. FIG. 2 shows the encircled energies $\Delta P_{Norm}(\theta_{i+1} - \theta_i)$ as a function of $$\frac{(\theta_{i+1} + \theta_i)}{2}$$

for effective diameters of 10 μm, 20 μm and 30 μm. The cloud of 20 m depth was set at a distance of 100 m from the lidar system. It was set to be homogeneous in particles size and concentration and fixed at an optical depth of 0.1. The backscatter measurement distance, $z_c$ was set at a distance of 150 m. FIG. 3 shows the encircled energies $\Delta P_{Norm}(\theta_{i+1} - \theta_i)$ as a function of $$\frac{(\theta_{i+1} + \theta_i)}{2}$$

for effective diameters of 30 μm for 3 sounding distances: 150 m, 180 m and 210 m; all the cloud parameters are the same as previously.

Each size and measurement geometry shows a maximum value of the scattered energy contained in a ring clearly separated from each other. We can establish mathematically the position of these maximums. From eq.9, we obtain the position of the maximum by setting the derivative of the integrant equal to zero; i.e.:

$$\frac{d\beta e^{-A_1^2 y^2 \beta^2}}{d\beta} = 0 \qquad [10]$$

This leads to:

$$\beta_{max} = \frac{\lambda}{d_{eff} \pi A_1 \sqrt{2}} = 1.30 \frac{\lambda}{\pi d_{eff}} \qquad [11]$$

This result is in very good agreement with the position of the maximum for diffraction; the constant being 1.375 vs 1.30 obtained from eq.11 (J. Swithenbank et al., 1976, *AIAA 14th Aerospace Sciences Meeting*, 76-69).

The maximum of the encircled energy $\Delta L(\beta_{i+1} - \beta_i)$ needs, however, to be transformed into the lidar FOV reference frame. This is done using the relation between the FOV and the scattering angle $$\left( \tan \beta_{max} = \frac{z_c \tan \theta_{max}}{z_c - z} \right)$$

with eq.11, replacing z by the value of the middle position of the bioaerosol cloud ($0.5*(z_a - z_b)$). Using the small angle approximation, we obtain:

$$d_{eff} = 1.30 \frac{\lambda}{\pi \theta_{max}} \frac{z_c - 0.5(z_a + z_b)}{z_c} \qquad [12]$$

When the intervals are distributed uniformly over a logarithmic scale using n intervals we can show that:

$$d_{eff} = 1.30\sqrt{2} \frac{\lambda}{\pi \theta_{max,Log}} \left[ \frac{\ln(1 + Cte)^2}{[(1 + Cte)^2 - 1]} \right]^{0.5} \frac{z_c - 0.5(z_a + z_b)}{z_c} \qquad [13]$$

where $$Cte = \left( 10^{(\log \beta_n - \log \beta_1) \frac{1}{n-1}} - 1 \right), \beta_1$$

and $\beta_n$ being the smallest and largest FOV considered. The term in bracket tends toward 1 when the number of segments tends toward infinity.

In the large FOVs, the laser beam contains energy due to its broadening by optical elements. This contribution is often ignored in multiple scattering measurements. However, because we are dealing with a very small amount of multiple scattered light, we cannot ignore the single scattering contribution coming from the laser beam profile. We consequently represent the laser beam with the sum of two Gaussian distributions with a divergence of $\psi_0$ and $\psi_1$. The second Gaussian distribution containing only a small fraction "f" of the total energy of the laser beam (typically a few percent) is used to represent the broadening of the laser beam by imperfect optics. The single scattering contribution to the measured scattered light in a FOV delimited by $\theta_i$ and $\theta_{i+1}$ can be written as $$P_{ss}(z_c, \theta_{i+1} - \theta_i) = \qquad \text{EQUATION 14}$$
$$P_s(z_c) \times \left[ (1-f) \left\{ \exp\left[-\frac{1}{2}\left(\frac{\theta_i}{\psi_0}\right)^2\right] - \exp\left[-\frac{1}{2}\left(\frac{\theta_{i+1}}{\psi_0}\right)^2\right] \right\} + \right.$$
$$\left. f \left\{ \exp\left[-\frac{1}{2}\left(\frac{\theta_i}{\psi_1}\right)^2\right] - \exp\left[-\frac{1}{2}\left(\frac{\theta_{i+1}}{\psi_1}\right)^2\right] \right\} \right].$$

The power contained in a ring is given by $$P(z_c, \theta_{i+1} - \theta_i) = P_{ss}(z_c, \theta_{i+1} - \theta_i) + P_D(z_c, \theta_{i-1} \theta_i) \qquad (15)$$

and the total power measured in a given FOV $\theta_{i+1}$ is given by $$P(z_c, \theta_{i+1}) = \sum_{i=1}^{i+1} P(z_c, \theta_{i+1} - \theta_i). \qquad \text{EQUATION 16}$$

The optical element quality will also affect the FOV light measurements dependence. The imagery performances will be worse in the larger FOVs since the number of aberrations increases with the FOV. However, the effect of imperfect optical components in our lidar system is considered to be small and it has not been taken into account since an off-axis parabolic mirror is used as the primary mirror telescope and the secondary optics is composed of achromatic lenses. This optical components choice has permitted us to maintain good optical quality over all the FOVs covered.

Thus, the instant technique requires two measurements: one in the presence of a bioaerosol cloud in the interval [$z_a$, $z_b$] and a second in its absence. The idea is to subtract the second signal from the first in order to minimize the effect of background aerosols and the laser beam profile on the bioaerosol size and concentration measurements. Also in order to avoid changes in the signal caused by the difference in transmission in the presence of the bioaerosol cloud and the laser pulse to pulse energy fluctuations we normalize the quantities with the single-scattering lidar return.

After dropping some parameters for compactness we obtain $$\Delta P_{Norm}(\theta_{i+1} - \theta_i) = \\ \frac{P_D(z_c, \Delta\theta_i, \alpha_b > 0) + P_{ss}(z_c, \Delta\theta_i, \alpha_b > 0)}{P_s(z_c, \theta_s, \alpha_b > 0)} - \\ \frac{P_D(z_c, \Delta\theta_i, \alpha_b = 0) + P_{ss}(z_c, \Delta\theta_i, \alpha_b = 0)}{P_s(z_c, \theta_s, \alpha_b = 0)},$$ EQUATION 18

Where $\theta_S$ corresponds to the angle used for the measurement of the single scattering signal and $\Delta\theta_i = \theta_{i+1} - \theta_i$.

FIG. 4 illustrates the experimental set-up used to validate the concept presented above in order to determine the size and concentration of low concentration bioaerosol clouds. Small amount of pollens (2 g and 4 g) were dispersed in DRDC Valcartier aerosol chamber. The aerosol chamber is 22 m long, 2.4 m high and 2.4 m wide. The interior is covered with black painted plywood panels. The opening of the doors, at both ends of the chamber, is electrically triggered. The doors collapse under gravity within 0.5 s.

The MFOV lidar used is the same as in Roy et al., 2004 although other suitable MFOV lidar arrangements known in the art may be used within the invention, as will be readily apparent to one of skill in the art. Specifically, it consists of a 100-Hz repetition rate Nd-YAG laser synchronized with a gated ICCD camera (Andor ICCD DH 720-18U-03). The characteristics of the outgoing laser beam are as follow: 2.5-cm diameter, 0.3-mrad divergence (50% total energy), linear polarization purity of 1/500, pulse energy in the atmosphere of 25 mJ, and pulse width of 15 ns. The primary optics consists of a 200-mm diameter off-axis parabolic mirror with a focal length of 760 mm. The position of the image plane is a function of the focal length and the object position. It is necessary to adjust the image plane position in accordance with the cloud distance. A quartz window is used to reflect parts of the backscatter light on a conventional lidar polarization detection module. A mask with a 1% transmission for FOVs smaller than 1.32 mrad and a 94% transmission for FOVs larger than 1.32 mrad is positioned at the image plane when required for greater dynamic range. This mask is made of a circular 0.5-mm thick BK7 glass disk of 12.5-mm diameter and has a central dot of 1 mm diameter with a high reflectivity (99.0%). The radial response of the whole system was characterized by a flat field measurement performed with a flat field box.

For each measurement event, we followed a procedure that allowed the optimisation of the camera acquisition speed and the reduction of the noise level, especially the readout noise. Initially, we determined the optimum number of pulses required on the camera chip before reading the CCD. Typically, we aimed for a maximum of 20,000 counts on a pixel (the saturation level is attained at 65,535 counts) to ensure enough lidar return on the photo-sensors matrix and a good linearity of the camera response. The light background was then measured just prior to acquiring the lidar return by opening the camera gate the same number of times as the lidar measurements. Finally, the background image was subtracted from the image of the lidar returns.

The measurements were acquired at night. A typical measurement sequence was as follows: The chamber doors were closed and the dissemination of aerosol performed. During dissemination and for 30 s after its completion, six small mixing fans located on the chamber floor were operated to ensure a good homogeneity inside the chamber. The doors were then opened and the ICCD camera begun measurements at the pre-selected distance with gate width of 20 ns and 60 ns sequentially. The pre-selected distance was chosen to ensure that the maximum of scattered energy in a ring was included in the camera FOV and that it was larger than the FOV containing the laser divergence. At the same time, a transmissometer was operated at a small off-axis angle from the lidar to give a reference value for the optical depth of the bioaerosol cloud disseminated. The optical depth of each of the ICCD measurement was calculated using:

$$\tau = -\ln\left(\frac{P(z_c, \theta_{min})}{P_{ref}(z_c, \theta_{min})}\right)^{1/2}$$ [19]

where $P_{ref}(z_c, \theta_{min})$ is the measured power in the absence of bioaerosol cloud.

Prior to disseminating pollens, the methodology has been verified using DUALITE™, a polymeric low density (0.13 g/cm³) microsphere material. The DUALITE M6001AE has a fairly narrow particle density distribution with an average diameter of 41 μm on a volume basis. The cloud was 10 m deep and its center was at a distance of 115 m from the lidar system. The backscattering sounding distance was set to a distance of 190 m and the gate width to 20 ns. FIG. 5a shows the normalized lidar return on background aerosols obtained when 2 g of M6001AE was disseminated inside the aerosol chamber; to its right, FIG. 5b shows the same measurement in absence of disseminated material inside the chamber. The center of these images was intentionally saturated to better observe the multiple scattering contribution. It is followed by the subtraction of FIG. 5b from FIG. 5a (FIG. 5c) and then on FIG. 5d by the image analysis in term of encircled energy in logarithmic spaced rings delimited by $\theta_i$ and $\theta_{i+1}$. The effective diameter was calculated using eq.13 using the position of the FOV corresponding to the maximum of scattered energy on a ring obtained by fitting a second order polynomial to the data points surrounding the maximum. The analysis leads to a measured $d_{eff}$ equal to 40.2 μm. This is in very good agreement with the manufacturer's specifications.

Following the DUALITE™ test, Elm and Timothy pollens were disseminated into the second half of the aerosol chamber. The clouds were 10 m deep and their centers were at a distance of 126 m from the lidar system. The tests were conducted with 2 g and 4 g for respectively a maximum possible concentration of 0.03 g/m³ and 0.06 g/m³. However, because of the pollens agglomeration at the exit of the dissemination device and the loss caused by sedimentation, the actual concentrations when the measurements were performed were significantly lower. The same type of analysis displayed in FIG. 5 was applied to the Elm and Timothy pollens for backscattering measurement for sounding distances of 158 m and 178 m respectively. Estimation of the optical depth was obtained using eq.19. Eight lidar measurements were taken for each of the pollens dissemination and the estimated optical depth obtained ranged from 0.01 to 0.05. The effective diameters retrieved for Elm and Timothy were (29.1±1.5) μm and (35.5±3.2) μm respectively. To validate these measurements, both pollens were observed under a microscope which revealed that their surfaces were rather regular and not quite spherical and that their size was ranging respectively from 24 to 30 μm and from 32 to 38 μm. The agreement between the microscope observation and the lidar measurement is very good. The optical depths retrieved using eq.19 were noisy and the transmissiometer stability is not sufficient to provide data for comparison for such small values of the optical depth. However, based on previous measurements realized with a greater amount of disseminated material in the aerosol chamber, we believe that the optical depths retrieved are representative.

For simulations, the aerosol number density distribution is represented with a trimodal lognormal distribution represented by the following equation:

$$\frac{dN(r)}{dr} = \sum_{i=1}^{3}\left(\frac{N_i}{\ln(10) * r * s_i * \sqrt{2\pi}}\right) \times \exp\left[-\frac{(\log r - \log r_i)^2}{2s_i^2}\right], \quad \text{EQUATION 20}$$

where $N(r)$ is the number density distribution of radius r, $s_i$ is the geometric standard deviation, $N_i$ is the relative number of particle for each mode, and $r_i$ is the mode mean radius.

Figure 6:
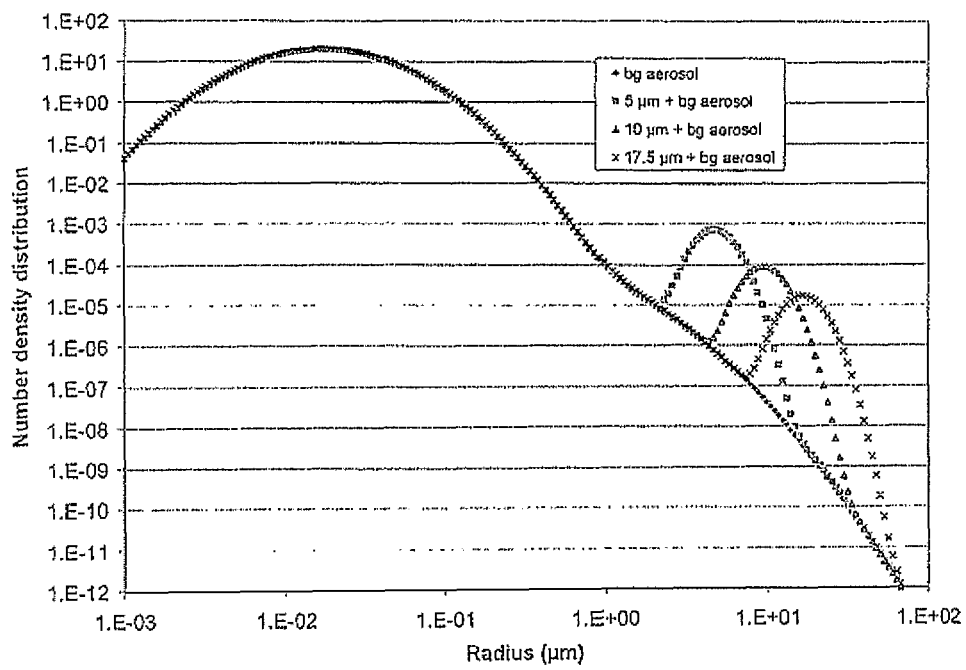

In our simulations, the background aerosol is a rural type with extinction a set arbitrarily to 0.00013 m$^{-1}$ (for a visibility of 30 km); it is represented by a bimodal lognormal distribution (Shettle and Fenn, 1979, Air Force Geophysics Laboratory Tech. Rep. AFGL-TR-79-0214). The bioaerosols are added as a third mode and its number of particles is chosen to give a total extinction of 0.00195 m$^{-1}$ over the bioaerosol cloud. So, a 10 m width cloud will have an optical depth of 0.02. FIG. 6 shows the number and volume particle size density distributions for an atmospheric aerosol of rural type at a relative humidity of 80% to which bioaerosols of 5, 10, and 17.5 μm radius have been added in the proportion specified in Table 1. The phase functions are calculated using Mie theory setting the refractive index to 1.42-i0.0123 and the distribution has been truncated at 100 μm. FIG. 7 shows the phase function as a function of the scattering angles ranging from 0° to 20° for the three particle distributions listed in Table 1. The phase functions are strongly peaked and clearly show their dependence over the size of the third. mode describing the bioaerosol size: the larger the ratio size-wavelength, the higher the peak.

Rayleigh scattering is also considered and the effective phase function is written as $p(\beta)=(\alpha_s p_\alpha(\beta)+(\alpha_R p_R(\beta))/(\alpha_s+\alpha_R)$; where $p(\beta)$ is the phase function obtained from application of Mie calculations on the particle size density distribution of interest and $p_R(\beta)$, $\alpha_R$ are the Rayleigh phase function and extinction. Their values are given by $p_R(\beta)=(3/16\pi)(1+\cos^2\beta)$ and $\alpha_R=1.33*10^{-5}*(\lambda/0.532)^{-4}$.

For all the simulations, 96% of the total laser energy is set at 532 nm and is contained in a Gaussian distribution with a divergence of $\psi_O=0.15$ mrad while the rest is contained in a second Gaussian distribution with a divergence of $\psi_1=2$ mrad. The minimum FOV considered is set equal to 0.1. mrad while the maximum is set to 6 mrad and the FOV space is divided into 31 elements evenly distributed over a logarithm scale.

One case studied reproduces the distances used for the experimental validation of the concept. FIG. 8 illustrates the single-scattering lidar return as a function of distance for the background aerosols including the contribution of a bioaerosol cloud extending from 120 to 130 m. We have also indicated on the graph the distances 140 and 178 m, which correspond to the backscattering measurement distances. For clarification purposes we have also indicated the lidar return in the absence of Rayleigh scattering. In short, the Rayleigh scattering is important and clearly enhances the backscattering at the wavelength we are considering. We are interested in the lidar signal as a function of the FOVs at the back of the bioaerosol cloud. FIG. 9 shows the calculated power as a function of FOVs for the 10, 20, and 35 μm mean diameter particles as well as the signal in the absence of bioaerosols, for a sounding distance $z_c$ equal to 178 m. At first look the four signals are quite similar and do not show noticeable changes as a function of FOVs. However a closer look reveals that, in the presence of bioaerosols, the signals are slightly lower since the laser beam is attenuated by the bioaerosol cloud presence. So, at first thought, one might consider that there is very little information that can be obtained from these signals. However, if the normalized background aerosol signal is subtracted from the normalized signal in the presence of bioaerosols, as shown in Eq. (18), very distinct signals are obtained. FIGS. 10 and 11 show $\Delta P_{norm}(z_c, \theta_{i+1}-\theta_i)$ as a function of 0.5 $(\theta_{i+1}-\theta_i)$ for sounding distances of 140 and 178 m and for the bioaerosol diameters of 10, 20, and 35 μm. The FOVs are equidistantly distributed on a log scale. FIGS. 10 and 11 show a clear dependence of $\Delta P_{norm}(z_c, \theta_{i+1}-\theta_i)$ over the bioaerosol size.

For another case, we consider a cloud situated between 995 and 1005 m with backscattered measurements performed at distances of 1025 and 1075 m. FIGS. 12 and 13 show $\Delta P_{norm}(z_c, \theta_{i+1}-\theta_i)$ as a function of FOVs for $z_c$ equal to 1025 and 1075 m, respectively. At 1025 m (FIG. 12) the peak for the 35 μm particles is absent, while the peak for the 20 μm particles is somewhat altered. However, if the measurement is taken at a greater distance, as in FIG. 13 where it is obtained at $z_c$=1075 m, the differentiation of the scattered light that occurs from the laser beam and the net peak described earlier becomes evident at shorter distances. Comparison of these two graphics clearly shows that it is not possible to obtain particle size information when the scatter energy is mixed up with the laser beam. The signals displayed in FIGS. 10-13 show that the position of the maximum encircled energy is dependent on the cloud distance relative to the lidar system and sounding distances as well as it is highly related to the bioaerosols size.

To understand these dependencies, we revisit Eq. (18). First, the ratios $P_{ss}(\alpha_b>0, \theta_{i+1}-\theta_i)/P_s(\alpha_b>0, \theta_s)$ and $P_{ss}(\alpha_b=0, \theta_{i+1}-\theta_i)/P_s(\alpha_b=0, \theta_s)$ are equal and cancel each other since the loss in transmission caused by the presence of bioaerosols vanishes with the normalization of $P_{ss}$ by $P_s(z_c, \theta_s)$. The normalization of the double-scattering signal with the single-scattering signal $P_s(z_c, \theta_s)$ leads to $$\frac{P_D(z_c, \theta_{i+1}-\theta_i)}{P_S(z_c, \theta_s)} = 2\int_0^{z_c} \alpha_s(z)\Delta L(r, z, \beta_{i+1}-\beta_i)dz. \quad \text{EQUATION 21}$$

Second, we break down the integral over z over three intervals: [0, $z_a$], [$z_a$, $z_b$] and [$z_b$, $z_c$] as illustrated in FIGS. 1b and 8:

$$\frac{P_D(z_c, \theta_{i+1}-\theta_i)}{P_S(z_c, \theta_s)} = 2\int_0^{z_a} \alpha_s(z)\Delta L(r, z, \beta_{i+1}-\beta_i)dz + \quad \text{EQUATION 22}$$
$$2\int_{z_a}^{z_b} \alpha_s(z)\Delta L(r, z, \beta_{i+1}-\beta_i)dz +$$
$$2\int_{z_b}^{z_c} \alpha_s(z)\Delta L(r, z, \beta_{i+1}-\beta_i)dz.$$

In the absence of bioaerosols, we have for the intervals $[0, z_a]$, $[z_a, z_b]$ and $[z_b, z_c]$:

$$\alpha_s(z)p(r,z,\beta) = \alpha_a(z)\omega_{0a}p_a(r,\beta) + \alpha_R p_R(r,\beta) \quad [5]$$

and in the presence of bioaerosols in the interval $[z_a, z_b]$ we have:

$$\alpha_s(z)p(r,z,\beta) = \alpha_a(z)\omega_{0a}p_a(r,\beta) + \alpha_b(z)\omega_{0b}p_b(r,\beta) + \alpha_R p_R(r,\beta) \quad [6]$$

where:
$\alpha_a$, $p_a(r, \beta)$ are the background aerosols extinction coefficient and phase function;
$\alpha_b$, $p_b(r, \beta)$ are the bioaerosols extinction coefficient and phase function;
$\alpha_R$, $p_R(r, \beta)$ are the Rayleigh scattering coefficient and phase function;
$\overline{\omega}_{0a}$ and $\overline{\omega}_{0b}$ are the respective single scatter albedo for background aerosols and bioaerosols.

Using eq.21, 22 and 23 and eq. 5 and 6 and subtracting the normalized background aerosols signal, we find $$\Delta P_{Norm}(\theta_{i+1} - \theta_1) = \quad [7]$$

$$\frac{P_D(z_c, \theta_{i+1} - \theta_i, \alpha_b > 0)}{P_s(z_c, \theta_s, \alpha_b > 0)} - \frac{P_D(z_c, \theta_{i+1} - \theta_i, \alpha_b = 0)}{P_s(z_c, \theta_s, \alpha_b = 0)} = 2\varpi_{0b}\int_{z_a}^{z_b}\alpha_b\Delta L(r, z, \beta_{i+1} - \beta_i)dz$$

This is the key equation that relates the normalized double-scattering measurement to the bioaerosols cloud optical depth and the encircled energy. It is independent of the background aerosols size and extinction as well as the laser beam profile for FOVs greater than the laser beam divergence. So, the calculation of $\Delta P_{norm}(\theta_{i+1} - \theta_i)$ can in principle provide information on the size and optical depth of bioaerosols.

The recovery of the bioaerosol size and extinction from the multiple scattering measurements is referred to as the inverse problem. Because we are dealing with very low concentrations and because we are able to eliminate the contribution of background aerosols, the signals are clean and show a strong and unique dependence over the size parameter. That is to say we will not deal with bimodal distribution.

However, in order to recover bioaerosol size information from Eq. (16), it is necessary to parameterize the phase function. We chose for that a unimodal size distribution of bioaerosols with a Gaussian fit using the concept of effective diameter as suggested by Bissonnette (1995):

$$p(\beta) = \frac{A_2}{\pi\omega_{0b}}y^2 e^{-A_1^2 y^2 \beta^2} \quad [8]$$

$$y = \frac{\pi d_{eff}}{\lambda}; A_1 = 0.544; A_2 = 0.139$$

where the effective diameter has been defined as a function of particles radius r as:

$$d_{eff} = 2<r^3>1<r^2>$$

After substitution in eq. 3 and using the small angle approximation, we get $$\Delta L(\beta_{i+1} - \beta_i) = \frac{2A_2 y^2}{\omega_{0b}}\int_{\beta_i}^{\beta_{i+1}} e^{-A_1^2 y^2 \beta^2}\beta d\beta \quad [9]$$

By substituting eq.9 in eq.7, considering a constant extinction cloud over z, and using the expression $\beta_i = z_c\theta_i/(z_c-\bar{z})$, where $\bar{z}=0.5(z_a+z_b)$, we get the following expression after integration over $\theta$:

$$\Delta P_{norm}(\theta_{i+1} - \theta_i) = 2\tau\frac{A_2}{A_1^2} \quad \text{EQUATION 23}$$

$$\left\{\exp\left[-A_1^2 y^2 \left(\frac{z_c}{z_c - \bar{z}}\right)^2 \theta_i^2\right] - \exp\left[-A_1^2 y^2 \left(\frac{z_c}{z_c - \bar{z}}\right)^2 \theta_{i+1}^2\right]\right\},$$

where $\tau$ is the bioaerosol cloud optical depth. Using Eq. (23), we have calculated theoretical values of $\Delta P_{norm}(\theta_{i+1} - \theta_i)$ for the bioaerosol size and cloud distance geometries already studied for the simulations illustrated in FIGS. 10-13. The model curves obtained have been identified with the extension Eq. (23). The agreement between simulation results and predictions obtained via Eq. (23) is quite good for the positions of the maximums. However, for FOVs greater than those associated with the peak position of $\Delta P_{norm}(\theta_{i+1} - \theta_i)$, the Gaussian model shows lower values since it takes into account only the diffraction component of the phase function and it neglects the geometric component of the phase function; which is independent of the particle size (Roy et al., 1997, Opt Eng 36: 3404-3415). Because our interest is in the position of the diffraction peak, the scattering geometric component has been deliberately ignored.

To retrieve meaningful information on the bioaerosols size from our model, we must establish a mathematical expression between the position of the $\Delta P_{norm}(\theta_{i+1} - \theta_i)$ peak, $\theta_{max, log}$, and the bioaerosol effective diameter. For uniformly distributed intervals over a logarithmic scale containing n intervals $$d_{eff} = 1.30\sqrt{2}\frac{\lambda}{\pi\theta_{max,Log}}\left[\frac{\ln(1+Cte)^2}{[(1+Cte)^2-1]}\right]^{0.5}\frac{z_c - \bar{z}}{z_c}, \quad \text{EQUATION 24}$$

Where $$Cte = \left(10^{(\log\theta_n - \log\theta_1)\frac{1}{n-1}} - 1\right),$$

$\theta_1$ and $\theta_n$ being the smallest and largest FOV considered. The term in bracket tends toward 1 when the number of segments tends toward infinity and is equal to 0.927 for the 31 FOVs used for the simulations.

Equation (24) is used to calculate the effective diameters of $\Delta P_{norm}(\theta_{i+1} - \theta_i)$ simulations displayed in FIGS. 10-13 using the position of $\theta_{max, log}$ obtained by doing a best fit with a second order polynomial on the $\Delta P_{norm}(\theta_{i+1} - \theta_i)$ data points surrounding the maximum. Once the effective diameter is known, the optical depth can be easily retrieved using Eq. (23). Tables 2 and 3 show the retrieved effective diameters and optical depths and their relative errors for the two cases studied. The optical depth retrieved value and error are shown in the last two columns. On average, for the clouds situated at the shortest distances from the lidar system, the relative error on the retrieved values is ~5% while for the cloud situated at 1000 m the retrieved values are 15% off the expected values. For the two cases simulated, it is not possible to retrieve the size of the bioaerosols. For the first case, at a distance of 178 m and for a bioaerosol of 10 μm in diameter the maximum occurs outside the sampled FOV; for the second case at a distance of 1025 m and for a bioaerosol of 35 μm in diameter, $\theta_{max, log}$ is less than or equal to the laser beam divergence and under those circumstances it is no longer possible to retrieve size information as well as the optical depth. In fact, the information at small FOVs is no longer available since the doubly scattered light is mixed with the laser beam.

We have shown that it is quite possible and relatively easy to recover size and extinction information from MFOV lidar simulations. However practically speaking, because we are dealing with small optical depths, the ratio of the power densities of the central region (where the laser beam is) over the scattered energy is very high. As an example, for an optical depth 0.005, the ratio of the unscattered energy over the scattered energy is 99. In addition if we consider that unscattered energy is contained within a FOV of 0.15 mrad and scattered energy is spread over 5 mrad (and completely recovered in the best case) the ratio of the power densities exceeds $10^5$. This exceeds the dynamic range of the instrument. That means that the central region of the detector will saturate before getting any significant signal on the larger FOVs. To overcome that problem, the central FOVs are attenuated with a mask of transmission $T_{mask}$. Specifically, the mask is arranged to be large enough to cover the laser beam size and the transmission is low enough to make the measured attenuated laser beam energy close to the measured scattered energy signal.

The MFOV lidar used is the same as described above: it consists of a 100 Hz repetition rate Nd:YAG laser synchronized with a gated intensified CCD camera (Ardor ICCD DH 720-18U-03). The characteristics of the outgoing laser beam are as follows: 2.5 cm diameter, 0.15 mrad divergence (half-angle including 50% of total laser energy), linear polarization purity of 1/500, pulse energy in the atmosphere of 25 mJ, and pulse width of 12 ns.

FIG. 14 shows the detection setup. The primary optics consists of a 200 mm diameter off-axis parabolic mirror with a focal length of 760 mm. The position of the image plane is a function of the focal length and the object position, and it is necessary to adjust the image plane position in accordance with the sounding distance. A quartz window is used to reflect part of the backscatter light on a conventional lidar polarization detection module. A mask with a 1% transmission for FOVs smaller than 1.32 mrad and a 94% transmission for FOVs larger than 1.32 mrad is positioned in the image plane when required for greater dynamic range. This circular 0.5 mm thick BK7 glass disk of 12.5 mm in diameter has a central dot of 1 mm diameter with a high reflectivity (99.0%). The radial response of the whole system was characterized by a flat field measurement performed with a flat field box.

The measurement technique requires two measurement events, one in the absence of bioaerosols to quantify the background aerosols and a second in the presence of aerosol cloud. For each measurement event, we followed a procedure that allowed the optimization of the camera acquisition speed and the reduction of the noise level, especially the readout noise. Initially, we determined the optimum number of pulses required on the camera chip before reading the CCD. Typically, we aimed for a maximum of 20,000 counts on a pixel (the saturation level is attained at 65,535 counts) to ensure enough lidar return on the photosensors matrix and a good linearity of the camera response. The light background was then measured just prior to acquiring the lidar return by opening the camera gate the same number of times as the lidar measurements. Finally, the background image was subtracted from the image of the lidar returns. Consequently, a total of four acquisitions are required to well-characterize the bioaerosols cloud.

The material is disseminated inside an aerosol chamber at a distance of 110 m from the lidar. The aerosol chamber is 22 m long, 2.4 m high, and 2.4 m wide. It was built of plywood panels painted black. The opening of the doors at both ends of the chamber is electrically triggered and the doors collapse under gravity within 0.5 s.

Elm and Timothy pollens have been disseminated into the second half of the aerosol chamber. The clouds were 10 m deep and their centers were at a distance of 126 m from the lidar system. The measurements were done at night under mild wind conditions. A typical measurement sequence was as follows. The chamber doors were closed and the dissemination of aerosols was performed. During and for 30 s after the end of the dissemination, six small mixing fans located on the chamber floor were operated to ensure a good homogeneity inside the chamber. The doors were then opened and the ICCD camera began taking measurements at the preselected distances with gates of 20 and 60 ns sequentially. The preselected distance has been chosen such that the maximum of the scattered energy in a ring is included in the camera's FOV and that it is larger than the FOV containing the laser divergence. At the same time, a transmissometer was operated at a small off-axis angle from the lidar to give a reference value for the optical depth of the bioaerosol cloud disseminated. FIG. 8 can be used to illustrate the experimental setup used to validate the concept proposed as well as the single scattering lidar return as a function of distances from the lidar.

The tests were conducted with 2 and 4 g for a maximum possible concentration of 0.03 and 0.06 g/m$^3$ respectively. However, because of the pollens agglomeration at the exit of the dissemination device and the loss caused by sedimentation, the actual concentrations when the measurements were performed were significantly lower. The optical depth for each of the ICCD measurements can be calculated from the simple ratio of the measured power, i.e., $$\tau = -\ln\left(\frac{P(z_c, \theta_{min})}{P_{ref}(z_c, \theta_{min})}\right)^{1/2} \quad [19]$$

where $P_{ref}(z_c, \theta_{min})$ is the measured power in the absence of bioaerosol cloud. It can also be calculated using the mask transmission $T_{mask}$ after the rearrangement of Eq. 24:

$$\tau = \frac{\Delta P_{Norm}(\theta_{i+1} - \theta_i) T_{mask}}{2\frac{A_2}{A_1^2}\left\{\exp\left[-A_1^2 y^2\left(\frac{z_c}{z_c - \bar{z}}\right)^2 \theta_1^2\right] - \exp\left[-A_1^2 y^2\left(\frac{z_c}{z_c - \bar{z}}\right)^2 \theta_{i+1}^2\right]\right\}}. \quad \text{EQUATION 25}$$

The measure of the optical depth based on power ratio is prone to errors for small optical depth retrieval because it is subject to laser power fluctuations. For example, a laser power fluctuation of 5% is sufficient to compromise measurement of an optical depth of 0.01 even though an average of 50 shots is used. Equation (25) offers the advantage of not being sensitive to laser shot to shot power fluctuations. However, it requires knowledge of effective transmission of the mask, $T_{mask}$. Estimation of the optical depth has been obtained using Eq. (25). Eight lidar measurements were taken for dissemination of each of the pollens and the estimated optical depths obtained range from 0.006 to 0.095. The optical depths retrieved using a simple ratio of the measured power were noisy and the transmissometer stability is not sufficient to provide data for comparison for such small values of the optical depth. However, based on previous measurements realized with a greater amount of disseminated material in the aerosol chamber, we believe that the optical depths retrieved are representative.

FIG. 15 shows the encircled energy $P(z_c, \theta_{i+1})$, as a function of FOVs for the Timothy and Elm pollens as well as their respective backgrounds. These measurements were obtained with the 1% transmission mask attenuating the small FOVs up to 0.66 mrad. The smooth transition between the small transmission region of the mask and its edge is caused by imperfections in optics, which cause the energy spreading in the image plane. FIG. 16 shows the measured normalized encircled energy $\Delta P_{norm}(\theta_{i+1}-\theta_i)$, for the Elm and Timothy pollens backscattering measurements for sounding distances of 158 and 178 m, respectively. The effective diameter is calculated using Eq (24). To validate these measurements, both pollens were observed under a microscope, which revealed that their surfaces were rather regular and not quite spherical and that their size ranged from 24 to 30 and from 32 to 38 µm. Table 4 shows a comparison of the mean diameter and standard deviation of the pollens as measured with the help of a microscope and the effective diameters retrieved with the MFOV lidar measurements. The agreement between the two measurement techniques is very good.

Accordingly, the recovering of particle parameters based on the measurement of multiple scattering is successful as long as the size of the particle of interest is compatible with the sounding wavelength of the laser, the FOVs used, the width of the cloud, and the sounding distances. Using Eq. (24) we can write the following constraint:

$$0.58 \frac{\lambda}{\theta_{FOVmax}} \left[ \frac{\ln(1+Cte)^2}{[(1+Cte)^2 - 1]} \right]^{0.5} \frac{z_c - \bar{z}}{z_c} < \quad \text{EQUATION 26}$$

$$d_{eff} < 0.58 \frac{\lambda}{\theta_{FOVmin}} \left[ \frac{\ln(1+Cte)^2}{[(1+Cte)^2 - 1]} \right]^{0.5} \frac{z_c - \bar{z}}{z_c},$$

where $\theta_{FOV\ min}$ and $\theta_{FOV\ max}$ correspond, respectively, to the smallest FOV (half-angle) containing almost all laser energy and to the largest FOV covered by the detector.

To fix ideas, we defined the constraint according to the parameters we have already used for the simulations described above. For the first case studied (see Table 2), a cloud at a distance of $\bar{z}$=125 m, studied with a lidar operating at 532 nm with FOVs (half angle) $\theta_{FOV\ min}$=0.5 mrad (to include most of the laser energy) and $\theta_{FOV\ max}$=6 mrad for sounding distances, $z_c$, ranging from 140 to 178 m, the effective diameter ranges that could be retrieved are within 5.5 and 178 µm. For the second case studied (see Table 3), for a cloud at a distance $\bar{z}$=1000 m for sounding distances, $z_c$, ranging from 1025 to 1075 m the retrievable effective diameter would be between 1.2 and 43 µm.

Depending on the applications there are measurement parameters that need to be optimized. Lidar systems that study cirrus clouds such as the high spectral resolution lidar (E. E. Eloranta, "High spectral resolution lidar", in Lidar: Range-Resolved Optical Remote Sensing of the Atmosphere, C. Weikamp, ed. Springer Series in Optical Sciences (Springer, 2005), 455 pp) are characterized by high-quality pointing stability and divergence beams as low as 50 µrad. For low optical depth cirrus clouds ranging from 9 to 10 km sounded with a lidar operating at 532 nm at distances ranging from 10.5 to 11, the retrievable effective diameters are included between 7 and 420 µm if we set $\theta_{FOV\ min}$=0.1 mrad and $\theta_{FOV\ max}$=4 mrad. If necessary, the sounded distance could be extended to 12 km and then the largest effective diameter that could be measured would be 642 µm. This is sufficient to cover the required range of effective diameters necessary for the successful recovery of cirrus cloud ice crystal particle size according to Eloranta (E. W. Eloranta, "Lidar multiple scattering models for use in cirrus clouds" in Twenty-First International Laser Radar Conference Proceedings, L. Bissonnette, G. Roy and G. Vallee, eds., (2002), pp 519-522). So, it should be interesting to use the subtraction technique we developed for the study and characterizations of cirrus clouds.

The dependence of the retrieved effective diameter on the ratio $(z_c-\bar{z})/z_c$, has a strong impact on the success and on the limitations of the inversion algorithm we developed. Considering the analysis of a cloud at a mean altitude $\bar{z}$ a given lidar system (so $\lambda$, $\theta_{FOV\ min}$, and $\theta_{FOV\ max}$ are fixed), the selection of the geometric factor $(z_c-\bar{z})/z_c$, can easily add a factor of 3 to the range of possible effective diameters that can be retrieved.

The described measurement method can be applied for clouds made of particles smaller than the wavelength. However, the equation that relates the effective diameter to the ratio of the wavelength over the maximum energy position $(\theta_{max,\ log})$, Eq. (24), is no longer valid because the mathematical expression used to parameterize the phase function is based on the diffraction effect. So, it is valid only for particle size greater than the wavelength. FIG. 17 shows $\Delta P_{norm}(z_c, \theta_{i+1}-\theta_i)$ as a function of $0.5(\theta_{i+1}-\theta_i)$ for a sounding distance of 4010 m. The clouds at the exit of a stack are within 3990 and 4000 m and are constituted of 0.2 and 1.0 µm in diameter particles for the two cases presented. The optical depth is 0.1 and all the other parameters describing the atmosphere and the lidar are the same as those used for FIGS. 10-13. For the particles smaller than the probing wavelength, the simulated $\Delta P_{norm}(z_c, \theta_{i+1}-\theta_i)$ exhibits a clear maximum at 1.7 mrad and the model based on diffraction shows a maximum at 3.25 mrad, while for the 1 µm particles the position of the maximum agrees fairly well. With proper parameterization of the phase function for particles smaller than the wavelength it should be possible the retrieve the effective diameter of particles smaller than the wavelength.

The current model is aimed at the standoff measurement of the effective diameter of a very small amount of bioaerosols. It is limited to second-order scattering and it is reliable for small optical depths. Contributions from scattering order higher than 2 will start to be noticeable for optical depths higher than 0.3 (Roy et al., 1999, Appl Opt 38: 5202-5211). Application of the present model to clouds with optical depth higher than 0.3 will require corrections and/or adjustments. Application of the measurement technique on clouds with optical depths ranging from 0.1 to 3 is required to study the problem. Monte Carlo simulations could be a suitable tool for that type of investigation.

Finally the experimental data have been obtained with an ICCD camera. It is not necessary to use an ICCD camera to do the measurements (G. Roy et al., 1998, "Efficient field-of-view control for multiple-field-of-view lidar receivers", in Nineteenth International Laser Radar Conference Proceedings, U. N. Sing, S. Ismail and G. K. Schwemmer, eds. (NASA/CP-1998-207671/PT2, 1998), pp. 767-770). Whatever technique is used, it is necessary to determine the FOV dependence of the sensor and to perform subtraction of the background radiation. It is also required that the measurement of the scattered light is done in the image plane, not at the focal point. The difference between the focal point and the image plane is particularly important when sounding distances get short. In that case, it could produce notable alterations in the shape of the signal measured in function of the receiver FOV that will affect the retrieved position of the $\Delta P_{norm}(\theta_{i+1}-\theta_i)$ peak and so the success of the method we developed. ICCD cameras present characteristics that make the measurements relatively easy. For example, they can be gated to match the laser pulse width, they are programmable, the number of FOVs and their values can be defined prior to the analysis of data, and the number of accumulations on the ICCD chips can be adjusted for the full dynamic range utilization of the camera.

While the preferred embodiments of the invention have been described above, it will be recognized and understood that various modifications may be made therein, and the appended claims are intended to cover all such modifications which may fall within the spirit and scope of the invention.

The invention claimed is:

1. A method of determining diameter of particles in a low concentration cloud or optical depth of a low concentration cloud comprising:

measuring scattering of a low concentration cloud comprised of particles of interest using a multiple field of view light detection and ranging (MFOV lidar) system, calculating the double scattering cloud signal and the single scattering cloud signal from said measurement and normalizing the double scattering cloud signal and the single scattering cloud signal, thereby providing a normalized cloud signal;

measuring scattering of a background region using a MFOV lidar system, calculating the double scattering background signal and the single scattering background signal from said measurement and normalizing the double scattering background signal and the single scattering background signal, thereby providing a normalized background signal;

subtracting the normalized background signal from the normalized cloud signal, and using said subtracted signal to calculate encircled energy of the particles within the low concentration cloud and optical depth of the low concentration cloud; and determining the effective particle diameter from the maximum encircled energy of the particles.

2. The method according to claim 1 wherein the cloud signal and the background signal are averaged.

3. The method according to claim 1 wherein the MFOV lidar system includes a transmission mask for attenuating central fields of view of the MFOV lidar system.

* * * * *